US009885012B2

(12) United States Patent
Grier, Jr. et al.

(10) Patent No.: US 9,885,012 B2
(45) Date of Patent: Feb. 6, 2018

(54) DEVICES, SYSTEMS, AND METHODS FOR TARGETED PLATING OF MATERIALS IN HIGH-THROUGHPUT CULTURE PLATES

(71) Applicant: AXION BIOSYSTEMS, INC., Atlanta, GA (US)

(72) Inventors: Robert Dixon Grier, Jr., Atlanta, GA (US); Anthony Michael Nicolini, Marietta, GA (US); Colin Michael Arrowood, Duluth, GA (US); Swaminathan Rajaraman, Atlanta, GA (US)

(73) Assignee: AXION BIOSYSTEMS, INC., Atlanta, GA (US)

( * ) Notice: Subject to any disclaimer, the term of this patent is extended or adjusted under 35 U.S.C. 154(b) by 239 days.

(21) Appl. No.: 14/533,373

(22) Filed: Nov. 5, 2014

(65) Prior Publication Data
US 2015/0125942 A1 May 7, 2015

Related U.S. Application Data

(60) Provisional application No. 61/899,970, filed on Nov. 5, 2013.

(51) Int. Cl.
*B01L 1/00* (2006.01)
*B01L 3/00* (2006.01)
*C12M 1/00* (2006.01)
*G01N 33/487* (2006.01)
*C12M 1/32* (2006.01)
(Continued)

(52) U.S. Cl.
CPC ............ *C12M 23/38* (2013.01); *C12M 23/00* (2013.01); *C12M 23/12* (2013.01); *C12M 33/04* (2013.01); *C12M 35/02* (2013.01); *C12M 41/12* (2013.01); *C12M 41/26* (2013.01); *C12M 41/32* (2013.01); *C12M 41/36* (2013.01); *C12M 41/46* (2013.01); *C12M 41/48* (2013.01); *G01N 33/48728* (2013.01)

(58) Field of Classification Search
CPC ..... B01L 2300/0627; B01L 2300/0636; B01L 3/502715; B01L 3/5027
See application file for complete search history.

(56) References Cited

U.S. PATENT DOCUMENTS 6,132,683 A * 10/2000 Sugihara ................ C12M 41/46
204/403.01
6,376,233 B1 * 4/2002 Wolf ..................... B01L 3/5085
204/403.01
(Continued)

*Primary Examiner* — Nathan Bowers
(74) *Attorney, Agent, or Firm* — Meunier Carlin & Curfman LLC

(57) ABSTRACT

Devices, systems, and methods for facilitating placement of cells and materials in culture plates configured for high-throughput applications are provided. A culture system is provided with a culture plate having a lid for guiding placement of cells and materials in each individual culture well of a culture plate. The lid may provide for coupling to an electrophysiology culture plate comprising a biosensor plate and a biologic culture plate, where the biosensor plate underlies and is coupled to the culture well plate such that each biosensor is operatively coupled to one culture well of the plurality of culture wells. A containment device that physically influences the positioning of fluid received in the culture plate is also provided herein.

19 Claims, 18 Drawing Sheets

(51) Int. Cl.
    *C12M 1/26*    (2006.01)
    *C12M 1/42*    (2006.01)
    *C12M 1/34*    (2006.01)
    *C12M 1/36*    (2006.01)

(56) References Cited

U.S. PATENT DOCUMENTS

| | | |
|---|---|---|
| 6,594,432 B2 | 7/2003 | Chen et al. |
| 6,733,968 B2 | 5/2004 | Yamamoto et al. |
| 6,852,525 B1 * | 2/2005 | Cantor .................. C12M 41/46 |
| | | 204/403.1 |
| 8,202,701 B2 | 6/2012 | Boyan et al. |
| 2004/0189311 A1 * | 9/2004 | Glezer ................. B01L 3/5027 |
| | | 324/444 |
| 2007/0072187 A1 | 3/2007 | Blok et al. |
| 2007/0231458 A1 | 10/2007 | Gale et al. |
| 2009/0205201 A1 * | 8/2009 | Xu ......................... C12M 23/12 |
| | | 29/825 |
| 2010/0304423 A1 | 12/2010 | Asai et al. |
| 2011/0269642 A1 * | 11/2011 | Glezer ................. B01L 3/5085 |
| | | 506/9 |
| 2012/0119750 A1 | 5/2012 | Morimoto et al. |

* cited by examiner

DEVICES, SYSTEMS, AND METHODS FOR TARGETED PLATING OF MATERIALS IN HIGH-THROUGHPUT CULTURE PLATES

This application claims priority to U.S. Provisional Patent Application No. 61/899,970, filed on Nov. 5, 2013, and hereby incorporated by reference in its entirety.

BACKGROUND OF THE INVENTION

Implementations described herein relate generally to devices, systems and methods enabling targeted plating of materials in high-throughput culture plates, and, more particularly, to culture well plates and lids configured to facilitate targeted placement of materials into an individual culture well.

In vitro electrophysiology culture systems having biosensors, such as microelectrode arrays (MEAs), can provide important insights into networks of electrically active cells. MEA-based electrophysiology culture systems can be configured to concurrently monitor single-cell and network-level activity over extended periods of time and without affecting the cell culture under investigation. Since their instrumental role in the landmark discovery of spontaneous waves in a developing retina, the variety and scope of MEA-based electrophysiology applications has dramatically expanded. Recently, for example, MEA-based electrophysiology culture systems have been used to investigate the suppression of epileptic activity and in the study of novel plasticity mechanisms in cultured neural networks. Advances in cell culture preparations have similarly led to applications for MEA-based electrophysiology culture systems in the fields of drug screening, safety pharmacology, and biosensing.

Present day MEA-based electrophysiology culture systems are typically designed around small-footprint, single-well devices. However, the complete analysis of complex cellular systems and processes can require repeated experiments. The number of experiments can increase quickly when considering multiple variables, such as, for example and without limitation, stimulus size, compound type, dosage strength and the like. Thus, the small-scale format of traditional MEA systems presents a "large N" problem (i.e., problems due to excessive experimental and statistical sampling sizes), whereby the serial nature of these devices can render even basic investigations time and cost prohibitive. As one illustrative example, a researcher examining the effect of pythrethroids on two-hour spontaneous activity recordings can require 8 doses of permethrin, with an N of 6 for each dose. With traditional MEA-based electrophysiology culture systems, this very simple experiment can require over $5,000 in MEA-based electrophysiology culture plates (or "MEA culture plates") and 50 to 60 man-hours. The time investment can further increase with the logistics of culturing, maintaining, and testing dozens of individual specimen.

The applicant has developed high-throughput MEA culture plates in an ANSI/SLAS compliant format to achieve industry compliance with other high-throughput instrumentation such as robotic handlers and plate readers. Such MEA culture plates are described in U.S. Provisional Patent No. 61/899,970, filed on Nov. 5, 2013, entitled "Devices, Systems and Methods for Targeted Plating Of Materials In High-Throughput Culture Plates," which is hereby incorporated by reference in its entirety. Such high-throughput culture plates can have well counts of, for example and without limitation, 12, 24, 48, 96, 192, 384 or 768. Further, each well plate can have an area of interest, e.g. an electroactive area that can be, for example and without limitation, about 1.25 mm to 2 mm in diameter.

SUMMARY

Plating cells and other materials (e.g., biomolecular coatings) can become a challenge when well counts are higher than about 12. Traditionally, materials are plated in such plates using pipetting—either manually or automatically. Manual plating can be cumbersome, time consuming, and inefficient. Automated plating with robotic handlers can be more efficient but also more costly than manual plating. Thus, even if utilizing automated plating, time and money can be saved by more accurately guiding the plating of cells and other materials. Accordingly, a need exists for improved devices, systems, and methods that enable targeted plating of cells and other materials in high-throughput culture systems.

Implementations described herein are directed toward devices, systems, and methods for facilitating placement of cells and materials in culture plates configured for high-throughput applications. Some implementations are directed to a culture system comprising a culture plate having a lid configured to guide placement of cells and materials in each individual culture well of a culture plate. Some implementations are directed toward culture wells with containment features or devices configured to concentrate the volume of the cells and other materials to a biosensor area.

DETAILED DESCRIPTION

Figure 1:
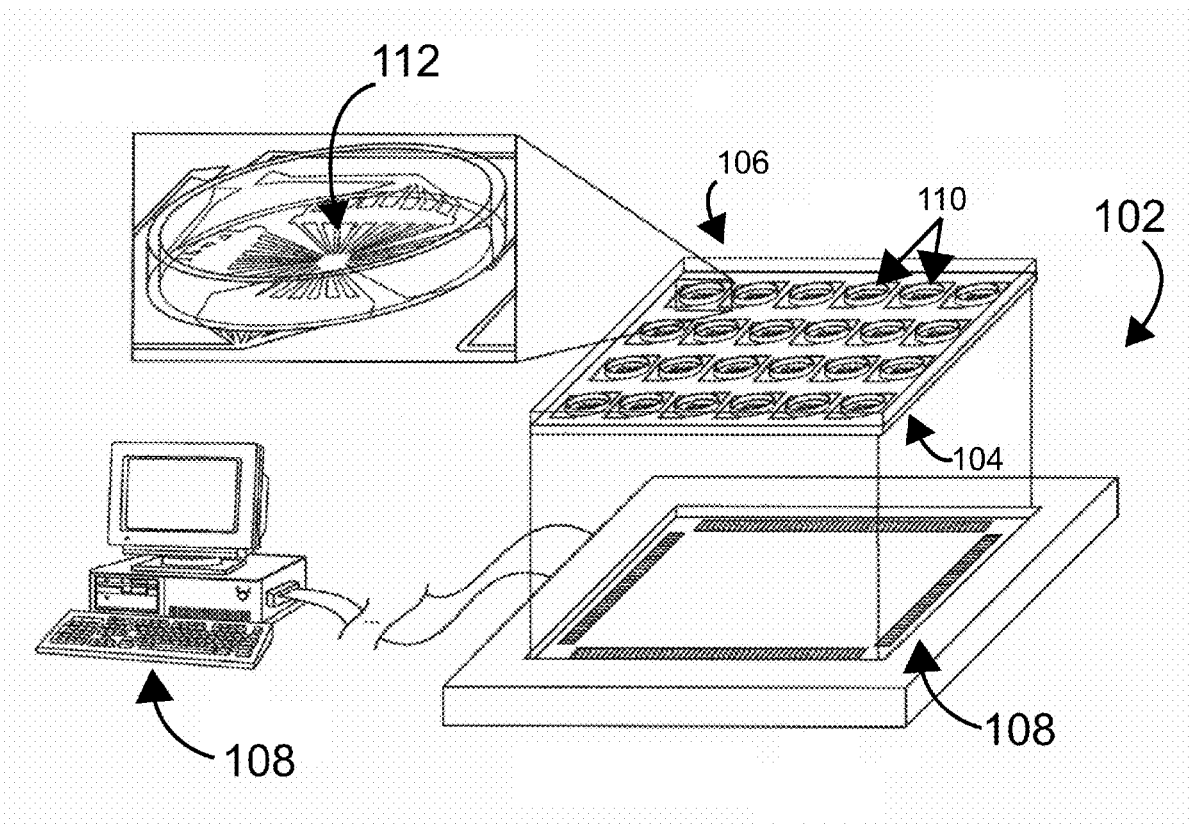
FIG. 1 is a schematic of an example embodiment of an electrophysiology culture plate and the associated electronics.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. The terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well-known aspects of electrophysiology culture systems, machining techniques, injection molding methodologies, and micro-electromechanical systems (MEMS) have not been described in particular detail in order to avoid unnecessarily obscuring aspects of the disclosed implementations.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be predefined it is understood that each of these additional steps can be predefined with any specific aspect or combination of aspects of the disclosed methods.

Implementations described herein are directed toward devices, systems and methods for facilitating placement of cells and materials in culture plates configured for high-throughput applications. More particularly, the present disclosure is directed to a culture system comprising a culture plate having a lid configured to guide placement of cells and materials in each individual culture well of a culture plate. For example, one or more implementations described herein provide for lid for coupling to an electrophysiology culture plate comprising a biosensor (such as a MEA) array plate having a plurality of biosensors and a biologic culture plate having a plurality of culture wells wherein the biosensor plate underlies and is coupled to the culture well plate such that each biosensor is operatively coupled to one culture well of the plurality of culture wells. As described herein, a biosensor may be a device used to measure electrical activity and to electrically stimulate a cell culture. For example, a biosensor may be an electrode or a microelectrode. A biosensor may also measure the pH, ionic concentration, impedance, strain, metabolite concentration, temperature, growth rate, proliferation rate, or any other measurable aspect of a cell culture.

Reference will now be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an example scale, but no inference should be drawn from the drawings as to any required scale.

High-throughput screening (HTS) tools make use of multi-well biologic culture plates that follow exacting guidelines established by the Society for Lab Automation and Screening (SLAS) and the American National Standards Institute (ANSI). These standards are adhered to by all HTS supporting equipment such as, for example and without limitation, plate readers, robotic handlers, liquid handling devices and the like. Compliance with these standards can enable a high-throughput biosensor platform to achieve full potential as it leverages existing high-throughput infrastructure including the automation of media exchanges and compound delivery.

In the following description, numerous specific details are set forth in order to provide a thorough understanding described herein. It will be obvious, however, to one skilled in the art that the present disclosure may be practiced without these specific details. In other instances, well-known aspects of electrophysiology culture systems machining techniques, injection molding methodologies and microelectromechanical systems (MEMS) have not been described in particular detail in order to avoid unnecessarily obscuring aspects of the disclosed implementations. Although a high-throughput electrophysiology culture system is described below for clarity, the culture well plate lids described herein are applicable to all other high-throughput culture plate systems.

Turning now to FIG. 1 in one embodiment, an electrophysiology culture plate 102 can comprise a monolithic biosensor plate such as a microelectrode array (MEA) plate 104 integrated with a biologic culture plate 106, and electronics 108 together with software configured to stimulate a cell culture via the electrophysiology culture plate to evoke a response and to record data. The electrophysiology culture plate can comprise a plurality of culture wells 110 configured to culture electroactive cells. A grid of tightly spaced microelectrodes 112 configured to extracellularly interface with the cultured cells may be operatively associated with each culture well 110. Each microelectrode or biosensor can be configured to record electrical activity from nearby neurons and electrically stimulate those cells. This technique can provide an extracellular, label-free method for examining both individual neuronal behavior and overall network activity, optionally, simultaneously. Mechanical features can also be provided that operate to couple the biosensor culture well plate 102 to the electronics 108. In a further aspect, these mechanical features can be configured so as not to interfere with topside access to the electrophysiology culture plate. In another aspect, the electronics unit can be used amplify and filter the low amplitude extracellular signals captured by both the microelectrodes and reference electrodes and, in other aspects, provide user directed stimulation to the cells. Reference electrodes can maintain a predetermined range or level of a given measurement, allowing for filtering of background noise from the microelectrode measurement. In some embodiments, a reference sensor may be a reference electrode that maintains a predetermined voltage range. For example, a reference sensor may be a ground electrode. In further aspects, the electronics unit can convert the analog electrode signals received from the cells into data that can be used and manipulated by the computer software, while minimizing the amount of noise injected into the very low amplitude signals that are measured (e.g., extracellular recordings).

Figure 2A:
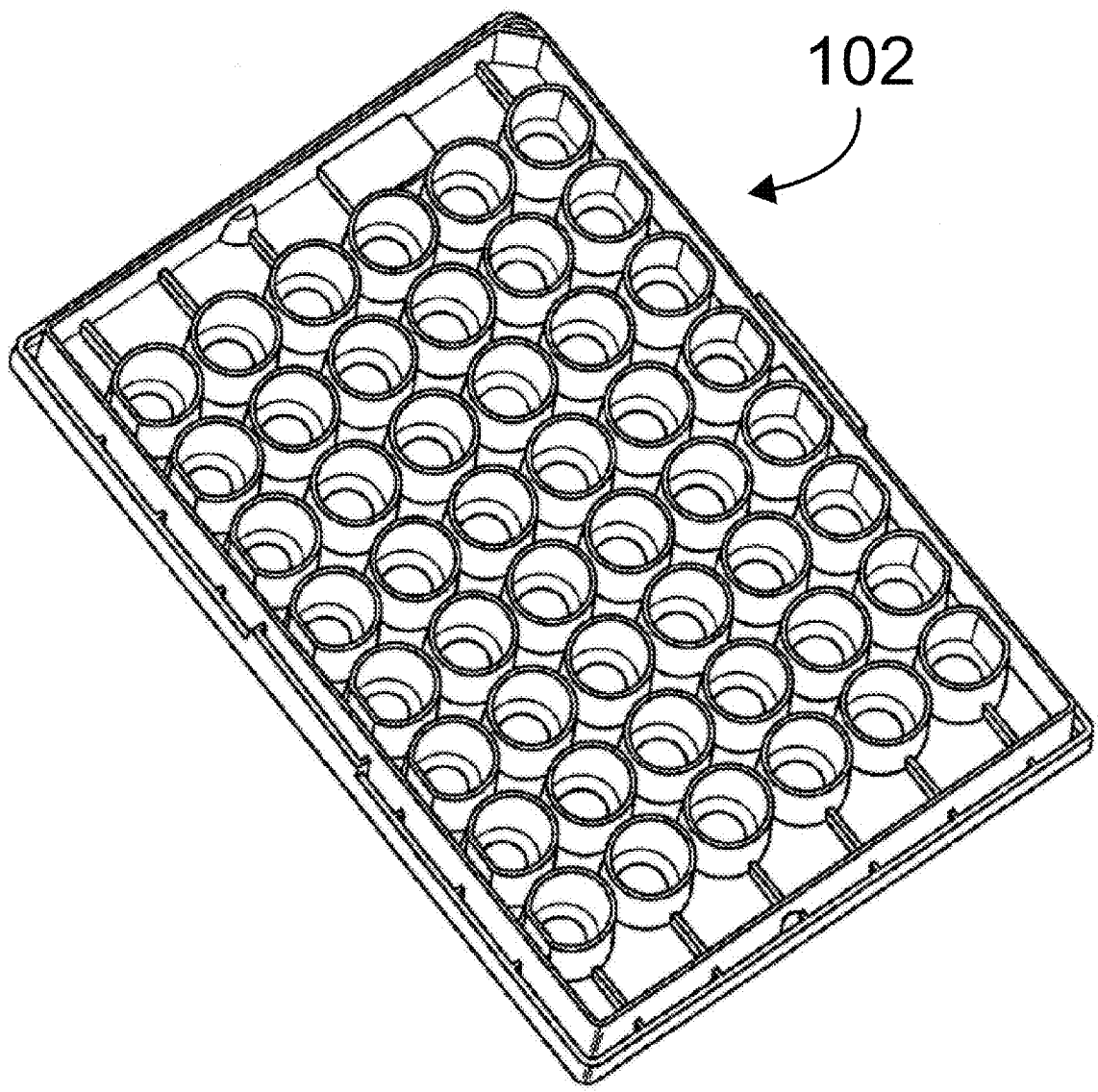
FIG. 2A is a schematic of an example embodiment of an electrophysiology culture plate.
Figure 2B:
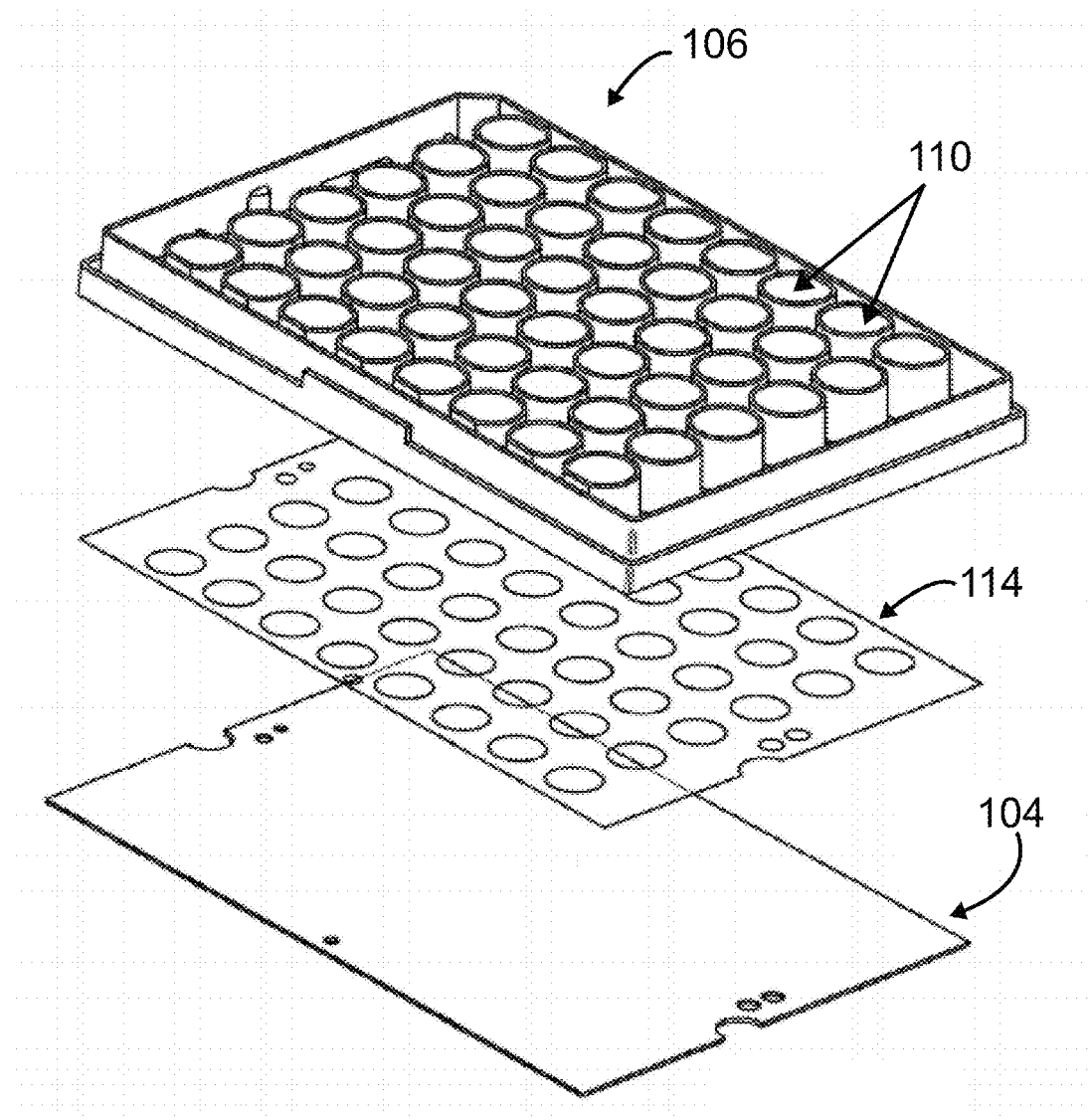
FIG. 2B is an exploded view of the electrophysiology culture plate from FIG. 2A.

The electrophysiology culture plate 102 shown in FIG. 2A can provide for high-throughput MEA culture well plates. FIG. 2B shows an exploded view of the electrophysiology culture plate, including a monolithic MEA plate 104 that can be fully vertically integrated with a culture well plate 106. In a further aspect, the monolithic MEA plate 104 and culture well plate 106 can be joined by an intermediate adhesive 114. The length and widths of the MEA plate 104 and adhesive material 114 may be sized to match the dimensions of the biologic culture plate 106. The overall size of the culture plate 106 may vary depending on the number and sizes of culture wells included on the plate. Any suitable size wells may be used, and any suitable culture plate size may be used as well. In some implementations, culture plate dimensions adhere to ANSI/SLAS microplate standards to achieve industry compliance with other high-throughput instrumentation such as robotic handlers and plate readers. Accordingly, it is a further aspect of this invention to provide culture well plates designed to provide at least 1 culture well. In some embodiments, the culture well plate may include at least 2, 4, 6, 12, 24, 48, 96, 384, 768, or more culture wells. In another aspect, a monolithic biosensor plate can comprise, for example and without limitation, polymers, glass, glass-reinforced epoxy resin, silicon, and the like.

In one aspect of the present disclosure, a multi-well biologic culture plate configured to be attached to the biosensor plate can be provided. In light of the present disclosure, one skilled in the art will appreciate that multi-well biologic culture plates may include micro-titer plates. In a further aspect, the biologic culture plate can comprise a lid. The biologic culture plate and lid can be formed, for example and without limitation, by conventional injection molding techniques. In a further aspect, the biologic culture plate and lid can comprise materials such as, for example and without limitation, polystyrene, polycarbonate, cyclic olefin polymer, cyclic olefin co-polymer, and the like.

Figure 3:
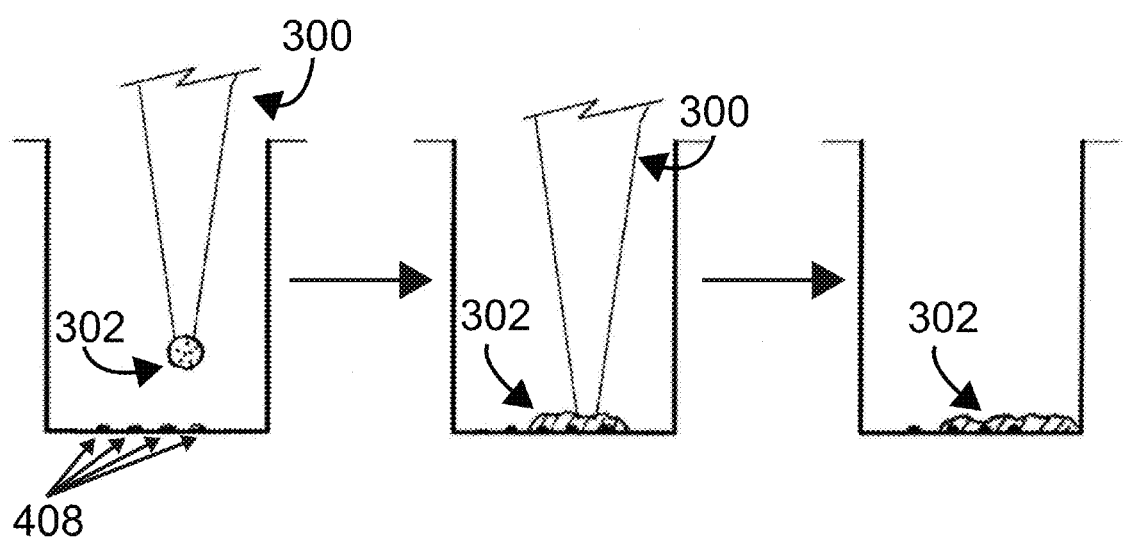
FIG. 3 is a step-by-step diagram of an example process of plating a cell suspension in an electrophysiology culture plate.

In other aspects, the present disclosure provides for culture well plate lids having extruded features designed to enable the ease of plating or spotting cellular suspensions and other materials either manually or in an automated procedure. Typical cell spotting or plating in an electrophysiology culture plate or a micro-titer plate can be performed without the use of a guide and as shown in FIG. 3. Such an unguided pipetting technique can be used both manually and via automated processes. As used herein, pipetting refers to the act of delivering liquid, semiliquid, or semisolid material to a well or surface. The term "pipette" may refer to any tool used to deliver the aforementioned material. As used herein, a pipette tip is the end of the pipette that dispenses the liquid, semiliquid, or semisolid material to a well or surface. Use of an unguided pipette 300 can be suitable in applications where the culture plate serves only as a support substrate for cellular growth and proliferation, thus precise placement of cells 302 and materials is not important. However, in many other cases the culture plate can be further functionalized with an electroactive area including without limitation biosensors, microelectrodes, microelectronics, impedance electrodes and the like. The biosensors 408 may be fabricated from gold, copper, platinum, nano-textured gold, nano-porous platinum, PEDOT, titanium nitride, indium tin oxide or any other suitable conductive material. For example, using biosensors 408 can enable stimulation and/or recording of cellular activity as well as engage the cell cultures in a variety of applications such as disease in a dish models, toxicity screening, phenotypic screening, stem cell characterization, and the like. Thus, when functional features are provided on a culture plate, precise placement or spotting of cells and other materials can become important.

Figure 4:
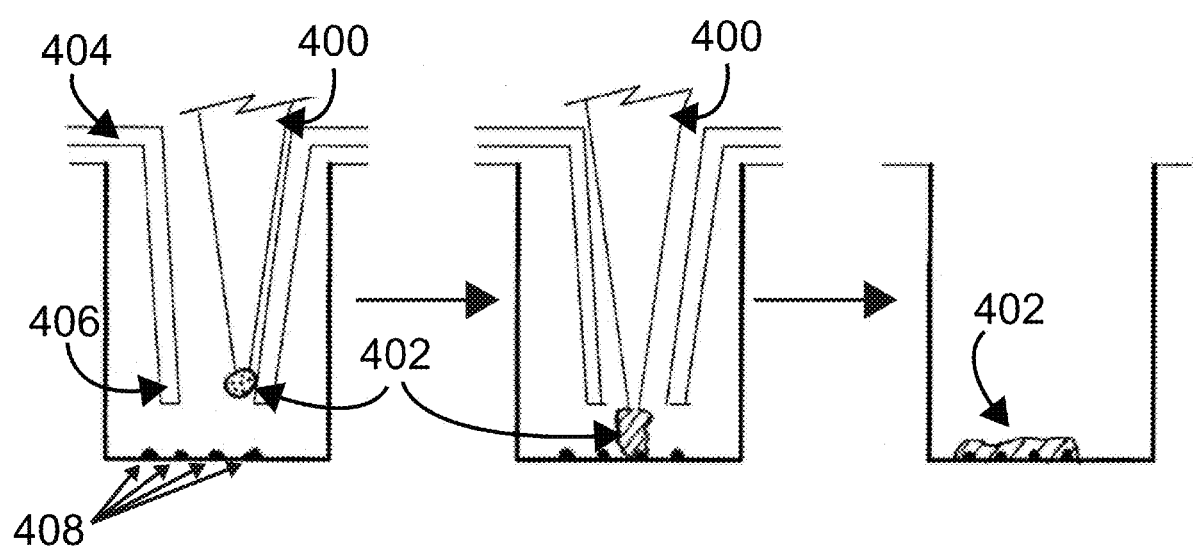
FIG. 4 is a step-by-step diagram of an example process of plating of a cell suspension in an electrophysiology culture plate guided by a targeted plating lid.

Accordingly and as shown in FIG. 4, it is an aspect of the present disclosure to provide for a culture well plate lid 404 that guides pipette 400 for targeted cell plating or spotting. The culture well plate lid 404 can comprise a plurality of targeting devices or extrusions 406 where each extrusion 406 has openings at its upper and lower ends and where the plurality of extrusions can be configured to mate with a plurality of culture wells present on a culture well plate. The extrusion 406 of the culture plate lid 404 guides the pipette 400 to a precise location (e.g., corresponding to biosensors 408) on the culture well plate thereby facilitating targeted deposition of cellular suspensions 402 and other materials. In one aspect, these extrusions can approximate micro to millimeter sized hollow frustocones, hollow pyramidal frustum, tubes, and combinations thereof. In another aspect, the height of the extrusions can range from about 1 mm to about 50 mm. In other embodiments the height of the extrusions may be about 11 mm to about 12.5 mm.

Figure 5A:
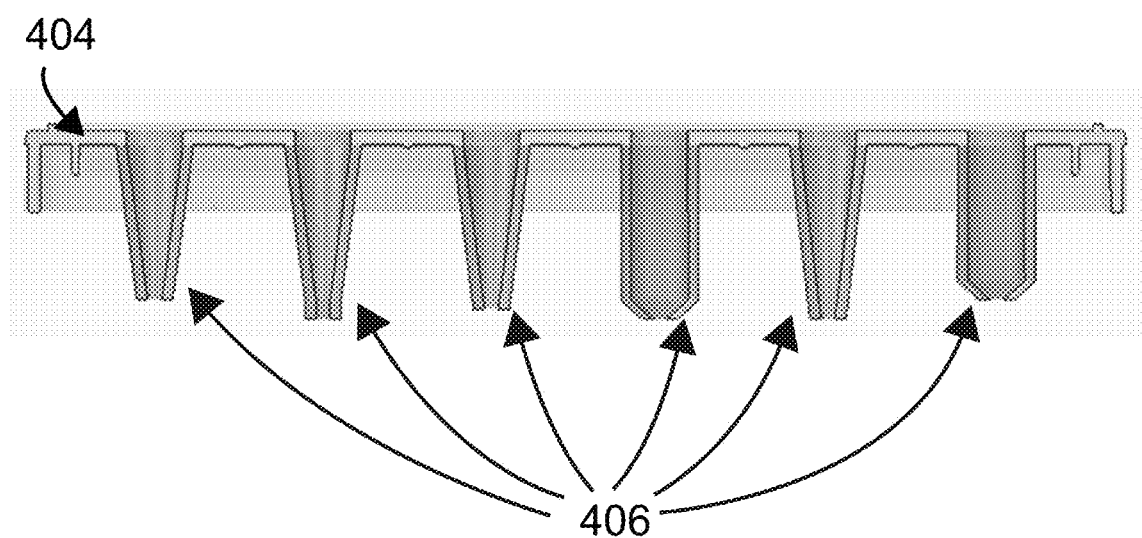
FIG. 5A shows a cross section of an example biologic culture plate lid with various targeting devices for guiding the plating of a cell suspension.
Figure 5B:
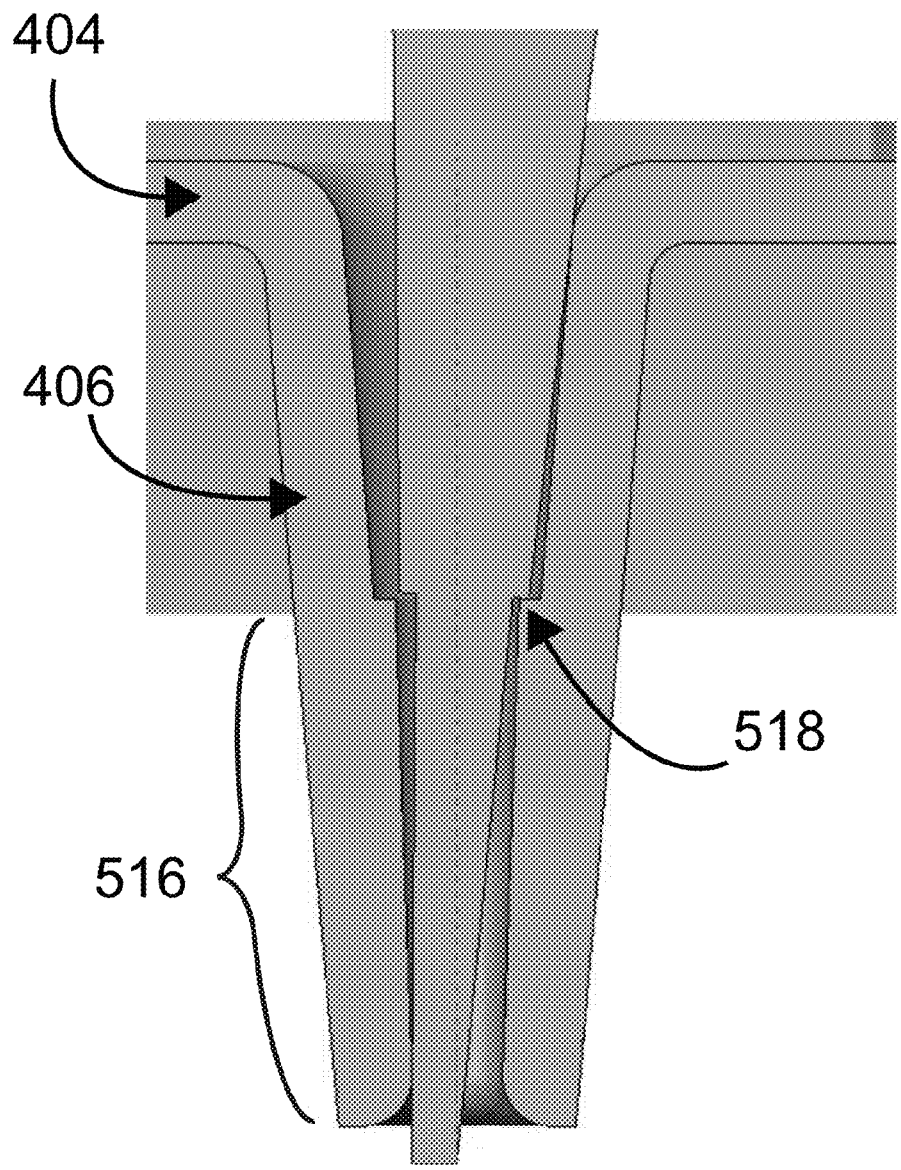
FIG. 5B shows a cross section of an example targeting device and a pipette.

FIG. 5A shows a lid 404 containing multiple implementations of targeting devices or extrusions 406. Culture well plate lids can comprise an array of extruded micro or milli-scale hollow frustocones or pyramidal or cylindrical frustum without or coupled with a tube at its distal end. A portion of the extrusion 406, labeled as tube 516 in FIG. 5B, may be shaped to form a collar 518. The collar 518 may engage a ridge on a pipette tip, preventing a portion of the pipette from extending beyond the collar 518. During the dispensing or placement of materials, collar 518 maintains a predetermined distance between a pipette tip and a biosensor array. In some embodiments, this predetermined distance may be 50 millimeters or less. In other embodiments, the predetermined distance may be 2.0 millimeters or less. In yet other embodiments, the predetermined distance may be 0.5 millimeters or less. However, any predetermined distance may be used, and the location of the collar 518 can be designed to provide any suitable distance. Collar 518 may also maintain a predetermined distance between the pipette tip and the distal end of the extrusion during the placement of materials. The location of collar 518 may influence this predetermined distance. The length of extrusion may also influence the predetermined distance. Any particular combination of collar 518 position and extrusion length may be used to provide the desired distance between the pipette tip and the distal end of the extrusion. As used herein, the distal end of an extrusion is the end located farthest from the rest of the lid 404.

FIG. 5A depicts a variety of types of extrusion profiles to illustrate different modalities of the present disclosure and, in practice, the culture well plate lid 404 would likely have a plurality of extrusions 406 having a uniform geometry. Although a variety of different extrusion profiles are shown here, the extrusions 406 are not limited to these profiles.

Figure 6A:
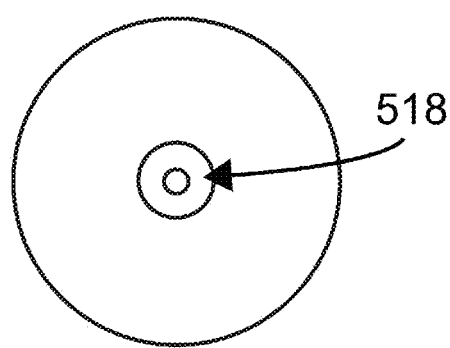
FIG. 6A is a top-down view of an example targeting device for guiding the plating of a cell suspension.
Figure 6B:
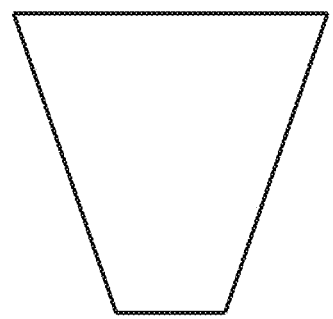
FIG. 6B is a side view of an example targeting device.

In some embodiments, the culture well plate lid can comprise at least one extruded micro- or milli-scale hollow frustocone. FIG. 6A is a top-down view of an example targeting device or extrusion 406. FIG. 6B is a side view of an example extrusion.

Figure 7A:
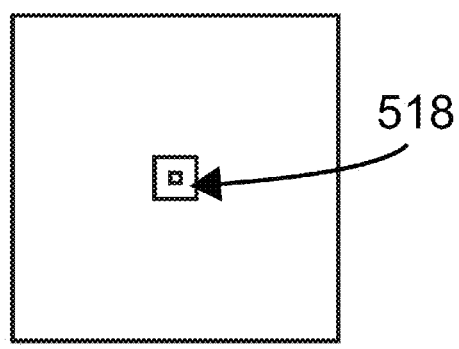
FIG. 7A is a top-down view of an example targeting device for guiding the plating of a cell suspension.
Figure 7B:
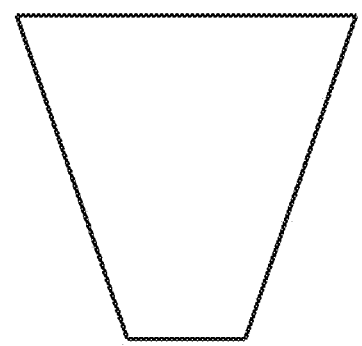
FIG. 7B is a side view of an example targeting device.

In other embodiments, the culture well plate lid can comprise at least one extruded micro- or milli-scale pyramidal frustum. FIG. 7A is a top-down view of an example extrusion 406, also including collar 518. FIG. 7B is a side view of an example extrusion.

Figure 8A:
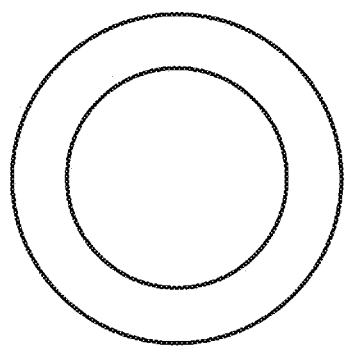
FIG. 8A is a top-down view of an example targeting device for guiding the plating of a cell suspension.
Figure 8B:
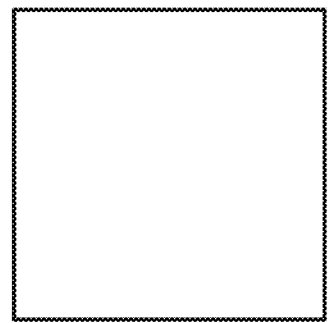
FIG. 8B is a side view of an example targeting device.

In another embodiment, the culture well plate lid can comprise at least one extruded micro- or milli-scale tube. FIG. 8A is a top-down view of an example extrusion 406. FIG. 8B is a side view of an example extrusion.

Figure 9A:
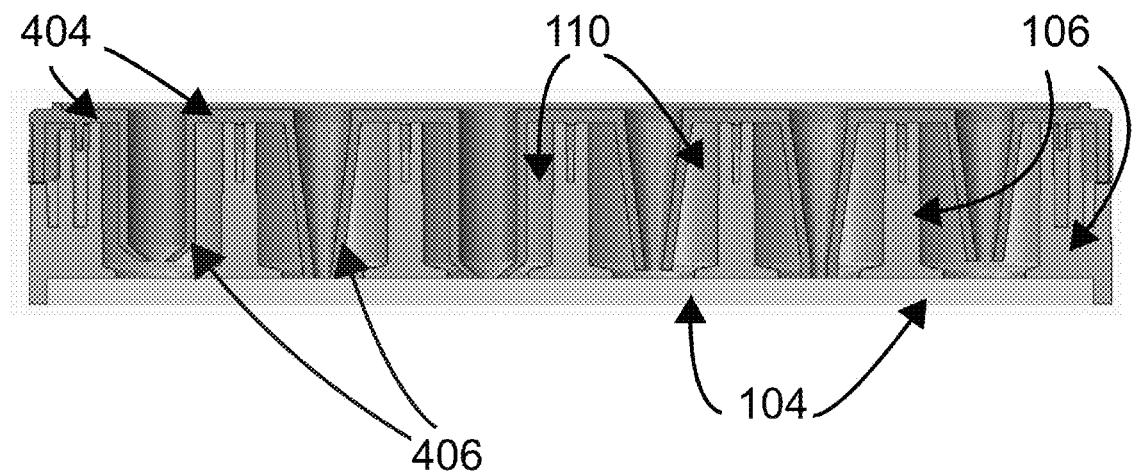
FIG. 9A shows a cross section of an example biologic culture plate lid attached to the biologic culture plate with a plurality of targeting devices.

FIG. 9A depicts an example culture well plate lid 404 coupled to a multi-well culture plate 106. The lid 404 includes targeting devices or extrusions 406 that extend into the wells of the culture plate 106. In this embodiment, the wells of culture plate 106 are spaced apart from one another such that there is material filling the space between the wells. In other embodiments, the wells may be closer together with thinner walls separating the wells. FIG. 9A also depicts a biosensor or MEA plate 104 attached to the bottom of culture plate 106. While this figure depicts a variety of types of extrusion profiles the lid 404 may also have a plurality of extrusions having a uniform geometry.

Figure 9B:
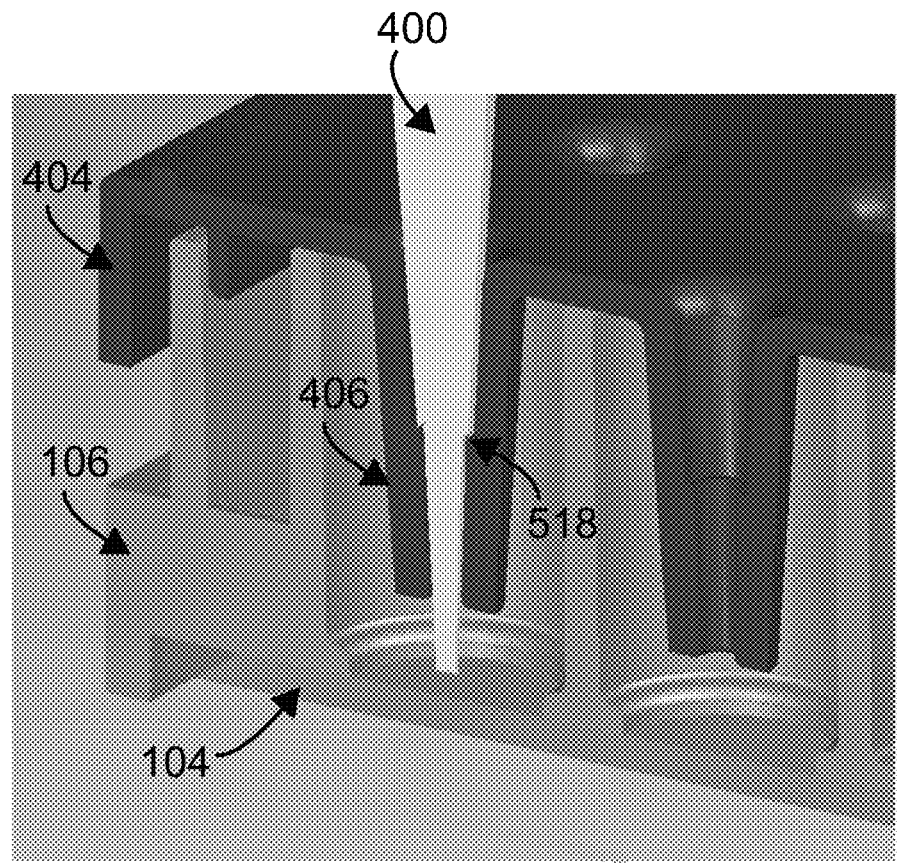
FIG. 9B shows a cross section of an example lid fitting onto an electrophysiology culture plate.

FIG. 9B shows another example embodiment of a lid 404 fitted into a multi-well culture plate 106. In this example embodiment, the lid 404 includes an extrusion 406 that incorporates a collar 518. Collar 518 is sized such that a pipette contacts the collar 518 after the pipette has been inserted into the extrusion 406 a sufficient distance. The collar 518 maintains a predetermined distance between a pipette tip and a biosensor array. Collar 518 may also maintain a predetermined distance between the pipette tip and the distal end of the extrusion during the placement of materials.

In various example embodiments, extruded frustocones, pyramidal frustum, tubes, and combinations thereof can serve as pipette tip guides for pipetting material and cellular suspensions into an area of interest. In one embodiment, the area of interest can be a biosensor or a biosensor array associated with the culture well plate. In one embodiment, the biosensor array can be an MEA. In other embodiments, pipetted materials can comprise biomolecular coatings such as, for example and without limitation, laminin, poly-ethylene imine (PEI), poly-ornithine, poly-L-Lysine, fibronectin and the like. In yet other aspects cellular suspensions can comprise, for example and without limitation, neural cells, cardiac cells, muscular cells, retinal cells, stem cells, and the like.

Figure 10A:
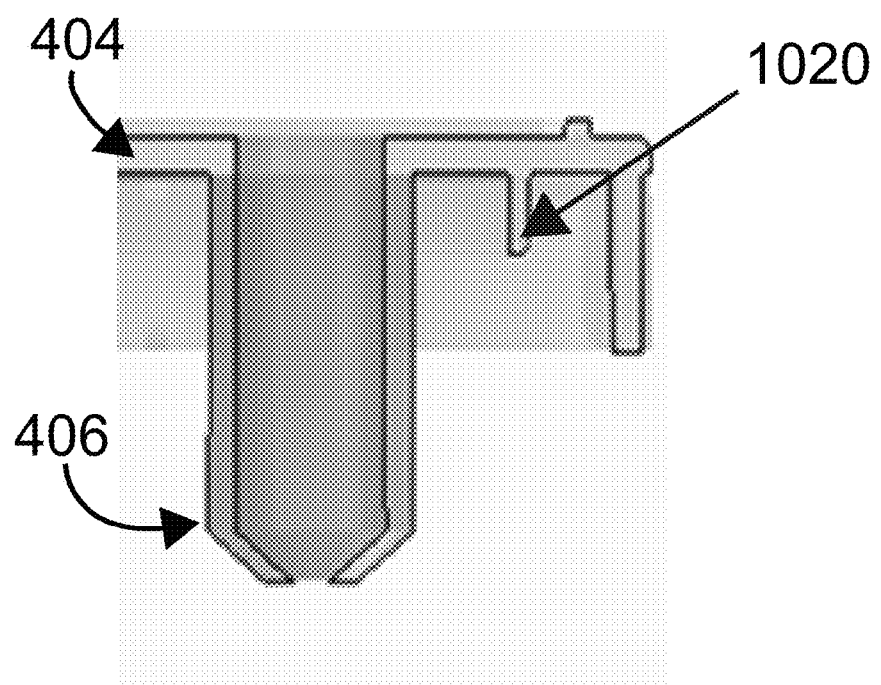
FIG. 10A shows a cross section of an example lid having a double baffle.
Figure 10B:
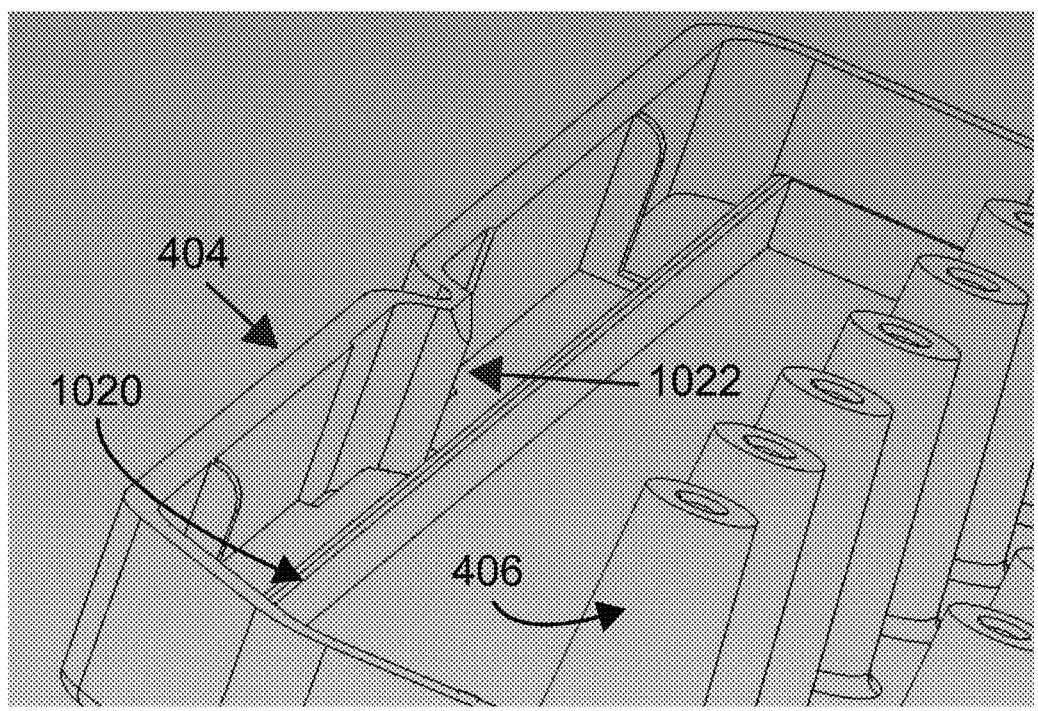
FIG. 10B is a perspective view of an example lid having a double baffle and a friction fit feature.
Figure 10C:
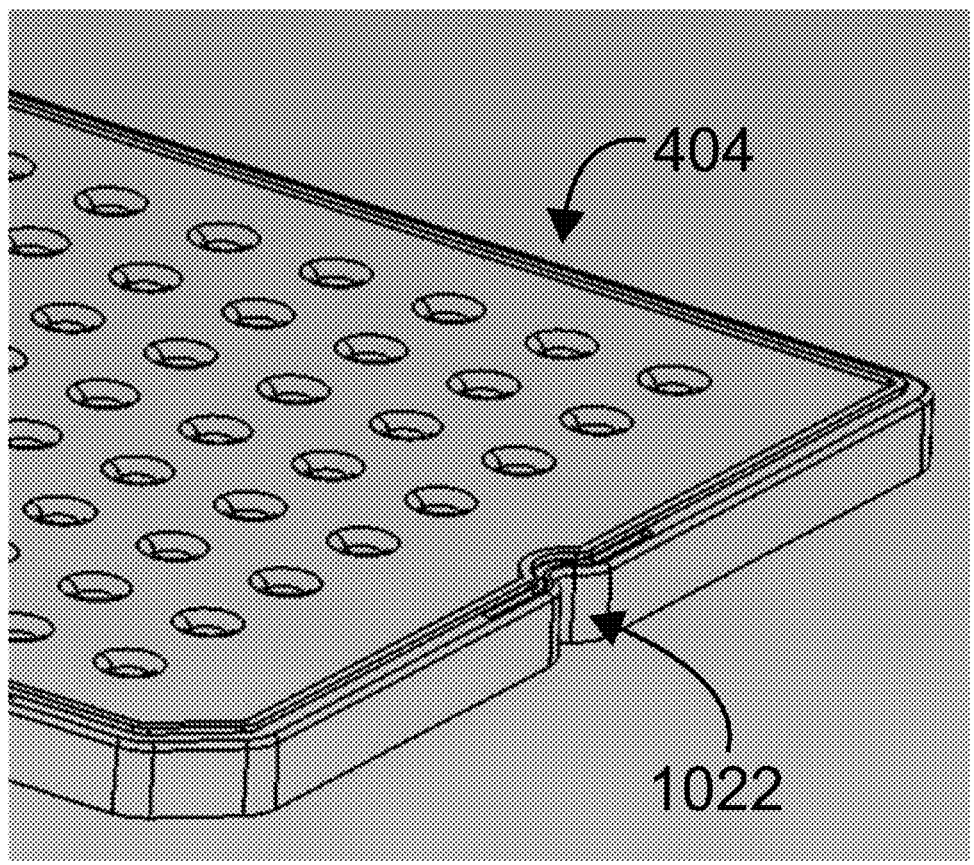
FIG. 10C is a perspective view of an example biologic culture plate lid having a friction fit feature.

FIGS. 10A-C show additional embodiments of lid 404. As seen in FIG. 10A, a cross section of lid 404, the edge may include a double baffled edge 1020 to reduce the amount of fluid lost through evaporation and/or maintain sterility within the culture plate. FIG. 10B shows a view of lid 404 turned upside down to better depict the features of this embodiment. In addition to the double baffled edge 1020, the lid may include a friction fit feature 1022. This feature flexes when pressed onto the culture well plate 106 and provides a source of friction that can function to keep the lid 404 securely on the well plate 106. It may also assist in holding the lid 404 in place while inserting and removing the pipette tip, further ensuring precise spotting of the cell suspension onto MEA plate 104. The friction fit feature also serves to locate the extruded shape to the center of the well. FIG. 10C is a top view of lid 404, further demonstrating the structure of an example embodiment of friction fit feature 1022.

Figure 11:
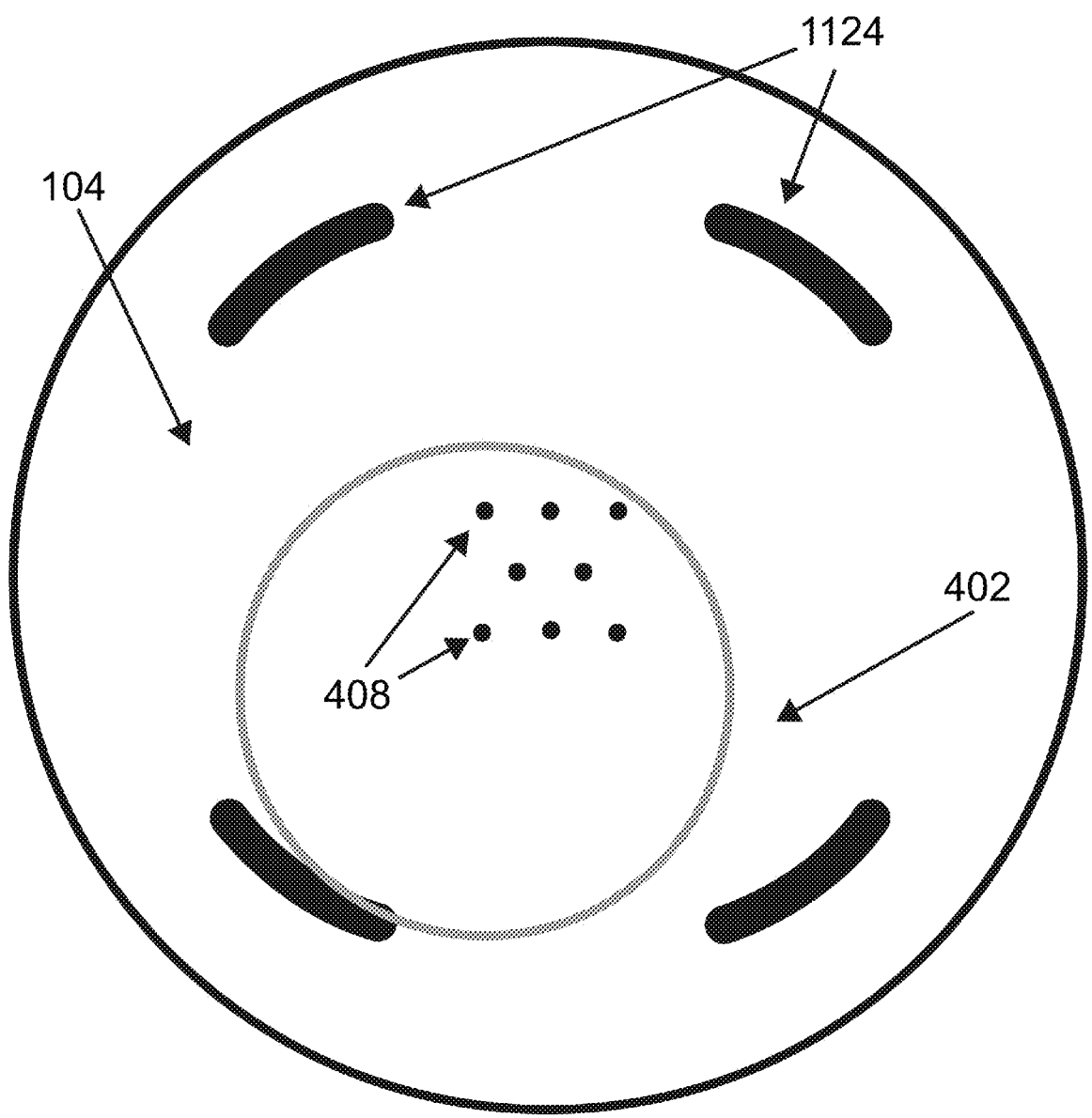
FIG. 11 shows a top-down view of an example culture well with biosensors and a mistargeted droplet.

FIG. 11 shows a top view of an example embodiment of a culture well 110 from a biologic culture plate 106 attached to a monolithic biosensor plate 104. In this example, a droplet of cell suspension 402 is mis-targeted and in contact with both with biosensors 408 and the reference sensors 1124, which may cause misinterpretation of the signals produced by the cells. In this embodiment, droplet 402 represents a 5-10 microliter drop of material. However, in other embodiments, droplet volume may be lower than 5 microliters or greater than 10 microliters.

Figure 12A:
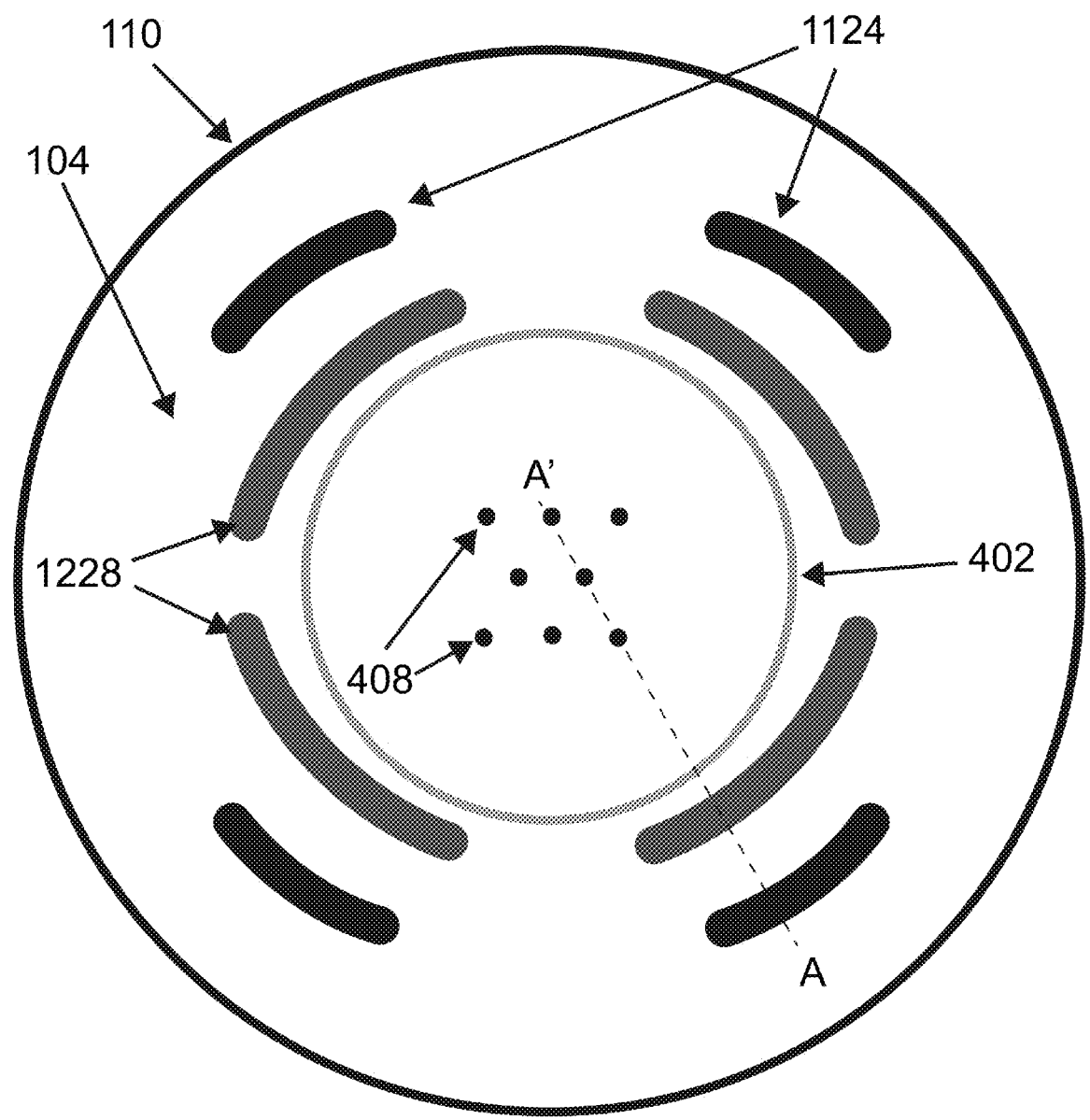
FIG. 12A shows a top-down view of an example culture well with biosensors and containment devices.

FIG. 12A shows a top view of an example embodiment of a culture well 110 with containment devices or features 1228 on the surface of the bottom of the well. Containment devices 1228 are configured to assist in the placement of materials by physically influencing the positioning of the fluid and concentrating the volume of the cells and other materials to the biosensors 408. In this embodiment, the containment devices are levees that are spaced between the biosensors 408 and the reference sensors 1124. In some embodiments, the levees are a minimum distance from the nearest biosensor 408, and a minimum distance from the nearest reference sensor 1124. The levees 1228 of the example shown in FIG. 12A are elongated in shape and follow the curve of the wall of the culture well 110. However, containment devices 1228 may take any shape and need not follow the curve of the culture well. For example, the containment devices 1228 may be rectangular, spherical, or any other shape that may assist in the placement of materials. In other aspects, containment devices may be moats, weirs, or any other structure designed to physically influence the positioning of the fluid.

The containment devices or features 1228 may physically influence the placement of materials by providing an object requiring a force for the material to surpass which is less than the surface tension that holds the material, such as a cell suspension, together in the center of the well. The height, shape, and structure of the containment devices 1228 may affect the extent to which they influence the positioning of the materials. For example, taller containment devices 1228 may be able to more effectively contain the materials, and may also be able to more effectively contain a greater quantity of materials, compared to shorter containment devices 1228. In addition, the number of containment devices 1228 can be varied depending on the volume, surface tension, and desired location of the materials being used in the well.

The containment devices 1228 may or may not be electrically active. In some implementations, the containment devices 1228 may be made from a metal including copper, gold, and so on. However, the containment devices 1228 may be made out of any materials that effectively accomplished a goal of, for example, containing the materials within the well.

Figure 12B:
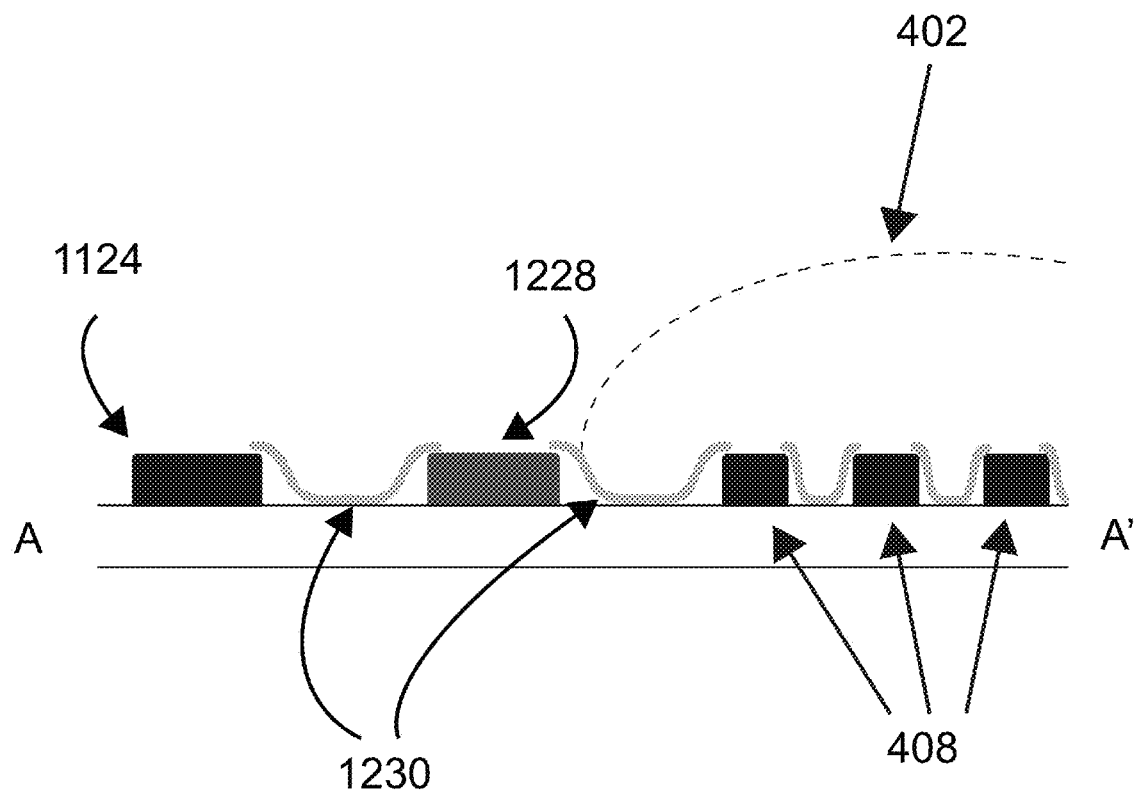
FIG. 12B shows a cross-sectional view along line A-A' of FIG. 12A.

FIG. 12B shows a cross section along line A-A' of FIG. 12A. In this embodiment, an insulating material 1230 is provided between the various biosensors 408, between the biosensors 408 and the containment device 1228, and/or between the containment device 1228 and the reference sensor 1124. The insulating material 1230 may be any suitable insulating material. In one embodiment, the insulating material 1230 is Kapton.

In one embodiment, a portion of the insulating material 1230 is adjacent to a containment device or feature 1228. As shown in FIG. 12B, the insulating material may slope upward from the bottom of the well plate to abut against one or more containment devices 1228, reference sensors 1124, and/or biosensors 408. The slope of the insulating material 1230 may physically prevent the spread of the cell suspension 402 toward the reference sensor 1124. In some embodiments, the insulating material 1230 further prevents spreading of the cell suspension 402 by hydrophobic interactions.

In one embodiment, the fabrication of the device includes a first step of layering an insulating material 1230 over the biosensors 408, reference sensors 1124, and containment devices 1228. The fabrication further includes a second step of removing portions of the insulating material to enable electrical communication between the cell suspension 402 and the biosensors. In certain embodiments, the fabrication includes a step of removing portions of the insulating material 1230 from the surfaces of the containment devices.

In some embodiments, culture well plate lids disclosed herein enable superior cell placement in an area of interest. In other embodiments, the culture well plate lids enable lower consumption of expensive reagents and cellular suspensions. In yet other embodiments, the signal-to-noise ratio during both stimulation and recording in an electrophysiology culture plate is improved due to placement directly on electroactive areas of the plate facilitated by the culture well plate lid. In some embodiments, the culture well plate lid facilitates isolation of the cellular suspension from the reference sensors.

The biologic culture plates and lids may be configured to be American National Standards Institute/Society for Lab Automation and Screening (ANSI/SLAS) compliant. For high-throughput culture systems such as electrophysiology culture systems, large-area, ANSI/SLAS-compliant high-throughput culture plate systems plates can be important as industry standard compliance can provide compatibility with other high-throughput instrumentation such as, for example and without limitation, plate readers, robotics handlers and the like. Such high-throughput culture plates can have well counts of, for example and without limitation, 1, 2, 4, 6, 8, 10, 12, 24, 48, 96, 192, 384 or 768, as well as a lid having, for example, 24, 48, 96, 192, 384, 768, or more corresponding extrusions.

In other aspects, the present disclosure can provide for electrophysiology culture plates that can be sterilized using simple treatments to eliminate the risk of cytotoxicity and do not require surface preparation (apart from standard biomolecular treatments) for cell culture applications.

In other aspects, the present disclosure provides for a culture well plate configuration: operable to prevent communication or contamination between adjacent wells. In a further aspect, the lid comprises a plurality of well caps configured to overlie each of the culture wells. In another aspect, each of the plurality of culture wells has the same height relative to the peripheral wall of the culture plate.

In other aspects, the present disclosure provides for culture well plates having culture wells configured to concentrate the volume of the cells/biomolecular treatments deposited specifically on the biosensor area. In yet other aspects, the present disclosure provides for culture well plates having culture wells comprising an upper diameter and a lower diameter, wherein the upper diameter is greater than the lower diameter. In a further aspect, the culture well can circumscribe either a conical or frustoconical structure on a lower portion of the well.

In another aspect, the biologic culture plate and biosensor plate contain at least one alignment feature configured to define the directionality of the plate or align the high-throughput culture well plate to a die-cut adhesive and the biosensor substrate or both. In a further aspect, once assembled, the alignment features also align the electrophysiology culture plate assembly to the docking mechanism and the high-density connectors located in the electronics unit.

Accordingly, FIGS. 1-12B, and the corresponding text, provide a number of different devices, systems, methods and mechanisms for high-throughput electrophysiology. In addition to the foregoing, implementations described herein can also be described in terms acts and steps in a method for accomplishing a particular result. For example, a method comprising at least one of plating, stimulating and recording data from a cell culture is described concurrently above with reference to the components and diagrams of FIGS. 1 through 9.

The present invention can thus be embodied in other specific forms without departing from its spirit or essential characteristics. The described aspects are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A culture plate comprising a plurality of wells for receiving fluid, wherein at least one of the wells comprises:
   a biosensor plate, wherein the biosensor plate defines a surface;
   a plurality of biosensors;
   at least one reference sensor;
   at least one containment device; and
   an insulating material, wherein the at least one containment device is located such that it physically influences the positioning of the received fluid, wherein the plurality of biosensors, the at least one reference sensor, and the at least one containment device are formed on the surface of the biosensor plate, wherein the insulating material is layered on at least a portion of the surface of the biosensor plate, wherein the insulating material and the plurality of biosensors create a varied topography on the surface of the biosensor plate, and wherein the at least one containment device is configured to concentrate the received fluid to the plurality of biosensors.

2. The culture plate of claim 1, wherein the at least one containment device is a levee.

3. The culture plate of claim 1, wherein the at least one containment device is electrically inactive.

4. The culture plate of claim 1, wherein the at least one containment device is electrically active.

5. The culture plate of claim 1, wherein the at least one containment device is located between at least one biosensor and the at least one reference sensor.

6. The culture plate of claim 1, wherein the insulating material is located between at least one biosensor and the at least one reference sensor.

7. The culture plate of claim 1, wherein the insulating material is located between at least one biosensor and the at least one containment device.

8. The culture plate of claim 1, wherein the insulating material is located between the at least one reference sensor and the at least one containment device.

9. The culture plate of claim 1, wherein the at least one containment device is metal.

10. The culture plate of claim 1, wherein the at least one of the wells comprises a bottom surface,
wherein a portion of the insulating material slopes upward from the bottom surface of the well.

11. The culture plate of claim 1, further comprising a hydrophobic insulating material adjacent the at least one containment device.

12. The culture plate of claim 1, wherein the plurality of biosensors, the at least one reference sensor, and the at least one containment device are exposed through the insulating material.

13. The culture plate of claim 1, wherein each of the plurality of biosensors is configured to record electrical activity from one or more cells and electrically stimulate the one or more cells.

14. A system for targeted placement of materials via a pipette, comprising:
the culture plate of claim 1; and
a lid shaped to removably couple to the culture plate, wherein the lid comprises a plurality of extrusions, wherein at least one of the extrusions extends into the at least one of the wells of the culture plate, and wherein the at least one of the extrusions is shaped to accept the pipette and direct contents of the pipette into the at least one of the wells.

15. The system of claim 14, wherein at least one of the extrusions comprises a collar configured to prevent a portion of the pipette from extending beyond the collar.

16. The system of claim 15, wherein the collar is configured to prevent a pipette tip from protruding more than a predetermined amount beyond a distal end of the at least one of the extrusions during placement of materials via the pipette.

17. The system of claim 15, wherein the collar is configured to maintain a predetermined distance between a pipette tip and the plurality of biosensors during placement of materials via the pipette.

18. The system of claim 14, wherein at least one of the extrusions is one of a frustoconical, cylindrical, and pyramidal shape.

19. The system of claim 14, wherein the lid comprises a friction-fit feature, the friction-fit feature configured to flex when in contact with the culture plate and removably secure the lid to the culture plate.

* * * * *

UNITED STATES PATENT AND TRADEMARK OFFICE
CERTIFICATE OF CORRECTION

PATENT NO. : 9,885,012 B2
APPLICATION NO. : 14/533373
DATED : February 6, 2018
INVENTOR(S) : Robert Dixon Grier, Jr. et al.

Page 1 of 1

It is certified that error appears in the above-identified patent and that said Letters Patent is hereby corrected as shown below:

In the Specification

In the first column, after the first paragraph at Line 7, please add the following paragraph:
STATEMENT REGARDING FEDERALLY FUNDED RESEARCH
This invention was made with government support under Grant no. R44NS062477 awarded by the National Institutes of Health. The government has certain rights in the invention.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*